United States Patent [19]
Coe et al.

[11] Patent Number: 5,902,247
[45] Date of Patent: May 11, 1999

[54] TRANSILLUMINATING CATHETER

[75] Inventors: Frederick L. Coe, Santa Barbara;
Michel Tuan Thien Tran, Ventura,
both of Calif.

[73] Assignee: BioEnterics Corporation, Carpinteria, Calif.

[21] Appl. No.: 08/926,140

[22] Filed: Sep. 9, 1997

[51] Int. Cl.⁶ .................................................. A61B 01/06
[52] U.S. Cl. .................. 600/476; 600/342; 600/478; 600/182; 606/15; 385/117
[58] Field of Search ..................................... 600/342, 476, 600/478, 121, 182; 606/14, 15; 385/117, 116, 119

[56] References Cited

U.S. PATENT DOCUMENTS

| | | |
|---|---|---|
| 3,819,442 | 6/1974 | Brushenko . |
| 4,268,112 | 5/1981 | Peterson . |
| 4,548,505 | 10/1985 | Ono . |
| 4,601,541 | 7/1986 | Shaw et al. . |
| 4,648,892 | 3/1987 | Kittrell et al. . |
| 4,938,205 | 7/1990 | Nudelman . |
| 4,952,022 | 8/1990 | Genovese . |
| 5,043,285 | 8/1991 | Surgi . |
| 5,066,292 | 11/1991 | Muller et al. . |
| 5,298,741 | 3/1994 | Walt et al. . |
| 5,304,173 | 4/1994 | Kittrell et al. . |
| 5,394,863 | 3/1995 | Sanford et al. . |
| 5,405,369 | 4/1995 | Selman et al. . |
| 5,423,321 | 6/1995 | Fontenot . |
| 5,449,354 | 9/1995 | Konwitz et al. . |
| 5,451,221 | 9/1995 | Cho et al. . |
| 5,517,997 | 5/1996 | Fontenot . |
| 5,665,051 | 9/1997 | Quick et al. . |

*Primary Examiner*—Marvin M. Lateef
*Assistant Examiner*—Shawna J Shaw
*Attorney, Agent, or Firm*—Michael G. Petit

[57] ABSTRACT

An apparatus and method for transilluminating a tubular tissue within the body. The apparatus comprises an elongate catheter having a fiber optic substantially coextensive with the length thereof which provides diffuse illumination laterally along at least a portion of the length of the catheter. The fiber optic terminus at the proximal end of the catheter is flared to form a light receiving aperture for collecting illuminating light. The flared proximal end of the optical fiber presents an effectively greater light input aperture and enables the fiber to conduct more light to the distal delivery end than would otherwise be possible with a fiber having a flat cut end and receiving light from a divergent light source. The distal end of the catheter is dimensioned to fit within a tubular tissue and be advanced therethrough. A portion of the distal end of the fiber optic is adapted to redirect the light laterally away from the optical axis along a length thereof to provide diffuse cylindrical illumination directed radially outward from the optical axis. The catheter is particularly adapted for transilluminating the wall of a length of a tubular tissue for visualization during surgical procedures such as laparoscopic surgery.

5 Claims, 2 Drawing Sheets

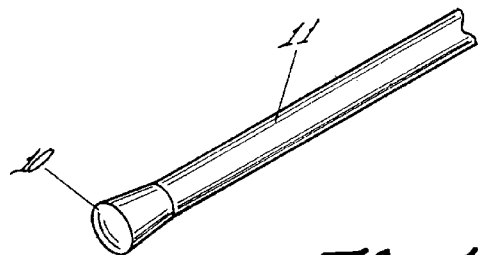
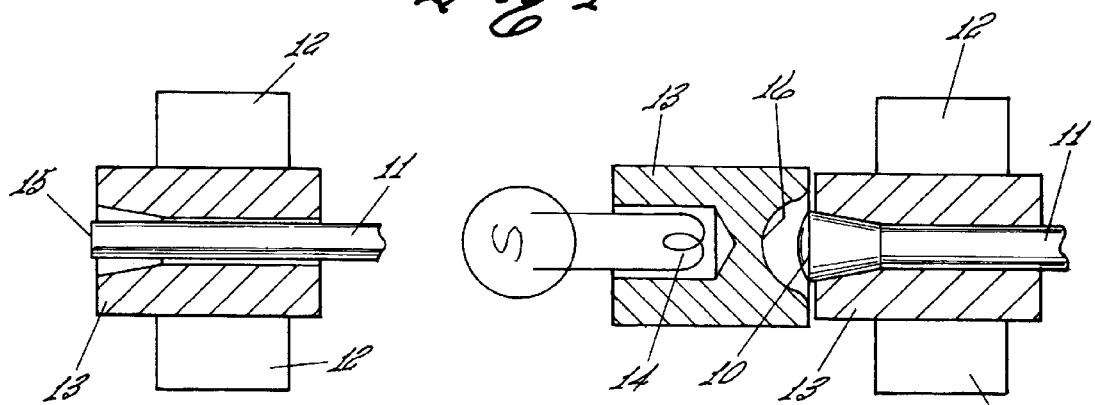
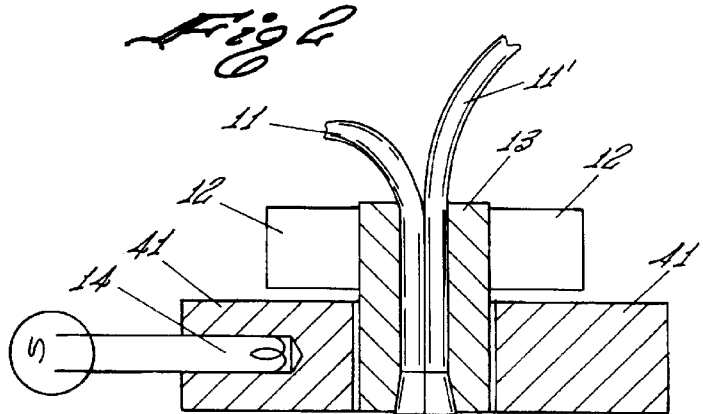
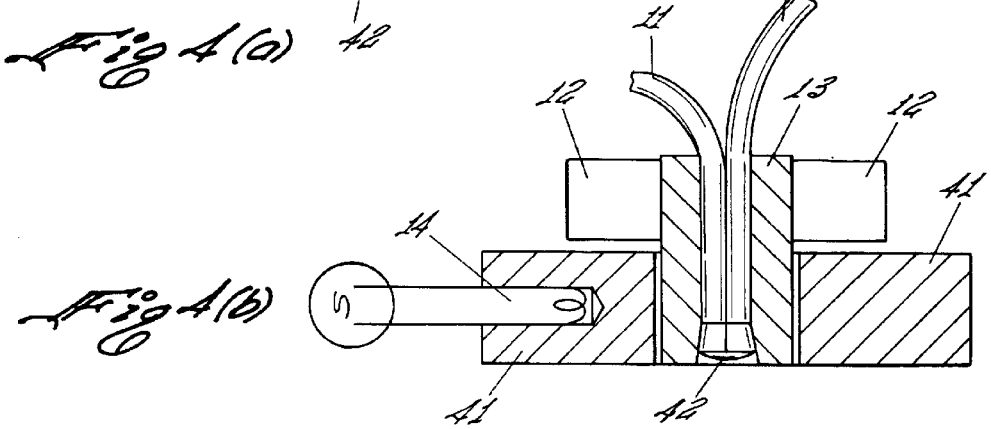

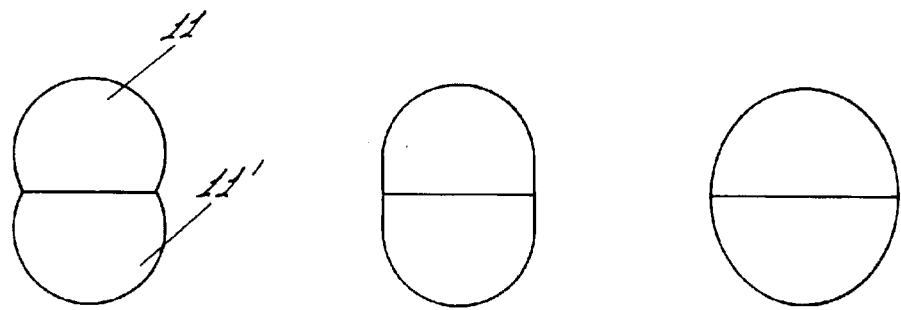
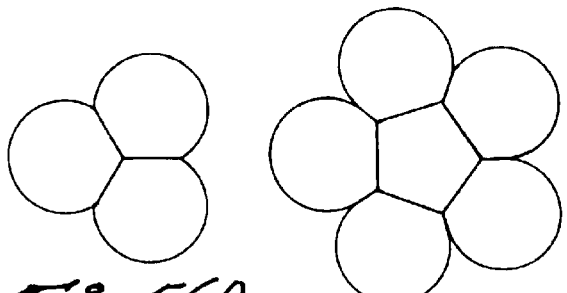
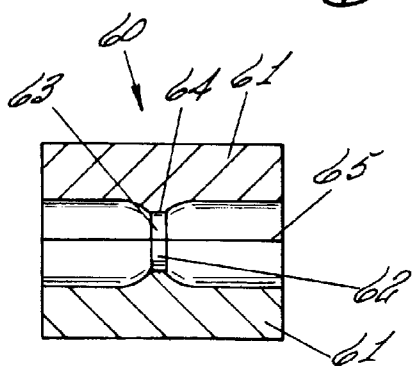
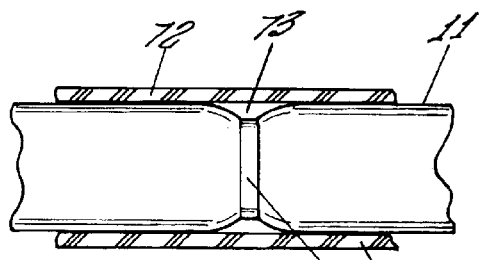
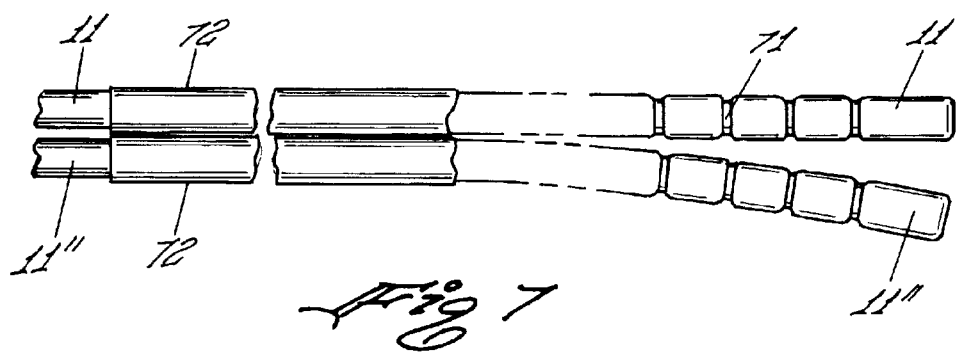

TRANSILLUMINATING CATHETER

BACKGROUND OF THE INVENTION

1. Field of the Invention

The present invention relates generally to a method and device for transilluminating a tubular tissue within the body of a patient.

2. Prior Art

Catheters such as transilluminating light delivery catheters, endoscopes, bougies and the like are frequently introduced into a lumen of the body for the purpose of transillumination. Such catheters include light delivery catheters having a diffuser tip on distal portion thereof. Such catheters are useful for delivering light to a distal portion of the body for performing phototherapeutic procedures as well as transillumination.

The majority of current standard operating room light sources have only a single light output port. Such sources are not designed for multiple catheter illumination. The operating room, therefore, must have a separate light source for each illuminator in more than one illuminator is to be employed in a procedure. There are a few light source manufacturers providing dual ports for dual illumination, however most multi-port sources permit only one catheter at a time to be attached thereto. Thus, if it is desired to have more than one tubular tissue transilluminated simultaneously, it is necessary to have more than one illuminating source to provide the power necessary for such transillumination.

Prior art fiber optics for illuminating small tissues have a relatively small cross-sectional diameter and the input end is flat cut to reduce reflection and loss of the input light from the source of light. The flat cut input aperture for such fibers limits the amount of light power which can be coupled into the catheter from a conventional non-collimated light source. In order to couple sufficient power into a light delivery catheter for certain applications such as transillumination, a complicated lensing system must be interposed between the light output port of the light source and the light input end of the fiber optic or fiber optic bundle within the catheter.

Martinez, in U.S. Pat. No. 5,437,290, provides a fiber optic having a flared proximal end suitable for collecting light from a single source of divergent or collimated light. The connector for attaching the proximal light-receiving end of the fiber to the light source requires collimating optics to be installed in optical alignment within the connector. In addition, the catheter can supply power to only a single fiber optic for transillumination.

During the performance of laparoscopic procedures such as surgery on or around the ureters, it is desirable to provide dual transillumination of the ureters in order to clearly visualize the operative field laparoscopically. In order to do so in accordance with the prior art, one must have separate delivery fibers attached to separate light sources threaded through the urethra into the bladder and transversing the ureters prior to initiating surgical procedures. It would, therefore, be desirable to have single optical fiber bundle which can be inserted the bladder through the urethra and which upon entry into the bladder could be made to bifurcate and diverge to form separate transilluminating fibers to simultaneously transilluminate both ureters from a single light source.

The Martinez patent referenced above contemplates a fiber optic having a proximal end which receives light from a rod having a flat face in optical communication with the proximal end of the fiber. The proximal end of the fiber optic is heated and shaped to form a lens. The lens is a-refractive lens; the radius or curvature of which is adapted to focus collimated light incident thereupon into the fiber optic for conduction along the length thereof to the distal end. The light incident upon the flared proximal end of the fiber optic is substantially collimated. It is desirable to provide a right delivery catheter wherein the light input end is adapted to receive light from a non-collimated source.

SUMMARY OF THE INVENTION

The present invention is a catheter for transilluminating the ureters with sufficient light intensity such that the ureters are visible to the surgeon during laparoscopic or open surgery. Such transillumination enables the surgeon to avoid iatrogenic injury to the ureters or other targeted tubular tissues during surgery. The present invention provides a catheter which permits transillumination of either individual or multiple tubular tissues using a single light source. In addition, the present invention also has improved light gathering capability when compared with a light delivery catheter presenting an unflared, light-receiving end as on a single, flat-cut fiber or a bundle of single fibers.

It is an object of this invention to provide an intralumenal catheter for transilluminating the wall of a tubular tissue.

It is another object of this invention to provide a device adapted to be inserted into a tubular tissue which can deliver improved power levels of light to transilluminate the tissue.

It is another object of this invention to provide a catheter wherein a single source of light can be used to transilluminate more than one tubular tissue.

It is another object of the invention to provide a fiber with discrete emitter zones operable for distributing transillumination or treatment light so that a higher light intensity may be delivered to a tissue without danger to a patient.

It is still a further object of the invention to provide a fiber with discrete emitter zones which are highly apparent in contrast to relatively dim surroundings, which emitter zones are easier to see than a continuously illuminated fiber surface.

The features of the invention believed to be novel are set forth with particularity in the appended claims. However, the invention itself, both as to organization and method of operation together with further object and advantages thereof may best be understood by reference to the following description taken in conjunction with the accompanying drawings in which:

BRIEF DESCRIPTION OF THE DRAWINGS

FIG. 1 is a perspective view of a fiber optic having a flared light-viewing end in accordance with the present invention.

FIG. 2 is a cross-sectional view showing the flat-cut proximal (light receiving) end of a fiber optic positioned within a flaring tool.

FIG. 3 is a cross-sectional diagram showing the relationship between a heating element and the flaring tool used to form a flared end on a fiber optic.

FIG. 4(a) is a cross-sectional schematic design of a flaring tool designed to fuse together the proximal light-receiving end of two or more fiber optics.

FIG. 4(b) is a cross-sectional schematic design of a flaring tool designed to fuse together the proximal light-receiving end of two or more fiber optics as in 4(a), showing the retraction of the proximal light-receiving end into the conical recess in the forming tool which occurs as fusion progresses.

FIG. 5(a) is an end-on view showing the shape of the light-receiving end of two fiber optics during fusion in accordance with FIGS. 4(a).

FIG. 5(b) shows another end-on view as in FIG. 5(a) wherein fusion of the proximal ends of the two fiber optics of FIG. 4(b) has progressed.

FIG. 5(c) shows the fusion as an end-on view as in FIGS. 5(a) and 5(b) wherein the forming tool has been maintained in juxtaposition to the fused ends for a different period of time and/or different temperature sufficient to complete the flaring and lens forming process at the light-receiving end of the optical fibers in accordance with the specific application for which the fused fiber optics are intended.

FIG. 5(d) is similar to 5(a) showing the end-on view of three fiber optics in the process of being fused.

FIG. 5(e) shows an end-on view of six fibers in the process of being fused.

FIG. 6 shows an cross-sectional view of a portion of a forming tool suitable for forming one or more annular grooves around the circumference of a single fiber optic near the distal light delivery end thereof FIG. 7 is a partially cutaway elevational view showing the discretely placed annular grooves on the distal end of a pair of fiber optics.

FIG. 8 is an enlarged view of a portion of the length of the optical fiber of FIG. 7 with the outer sheath positioned to create and maintain an air space overlying the annular groove(s), which is useful for directing light out of the fiber optic.

DESCRIPTION OF THE PREFERRED EMBODIMENTS

A simplified schematic view of a light delivery catheter having a flared focusing tip on the proximal light-receiving end of an optical fiber 11 is shown in FIG. 1. Turning now to FIGS. 2 and 3, an optical fiber 11 is inserted into a holding tool 12. A lens forming tool 13 having a heating element 14 in thermal communication therewith is positioned adjacent to the protruding end 15 of the fiber 11 to fuse the end 15 by radiant heating. The fused end of the fiber substantially conforms to the shape of a concave recess 16 in the adjacent end of the lens forming tool 13 by forming a meniscus. After forming, the lens forming tool 13 with the heating element 14 retracted and the optical fiber 11 removed from the forming tool 13.

FIG. 4(a) and 4(b) show a different arrangement of the holding and lens forming tools of FIGS. 2 and 3 specially adapted to accommodate two fibers. The proximal light-receiving ends of the optical fiber 11 and 11' are inserted through a bore within the forming tool 13. The fiber 11 and 11' with forming tool 13 are advanced into a holding tool 12. A heating element 14 embedded within the heating tool 41 heats the forming tool 13 to heat the end portions of the fibers 11 and 11' to near their melting points. The material comprising and retracting the fibers 11 and 11' flows to conform to the shape of the bore within the forming tool 13 which is funnel-shaped at the end of the bore through which the ends of the fibers 11 and 11' protrude. A curved meniscus forms a convex lens 42 when the heat is removed and the fused, flared ends are permitted to cool. After cooling, the fused light-receiving ends bearing the convex lens 42 retracts within the bore of the holding tool 12.

FIG. 4(b) shows the completed flaring, fusion and lens forming process in accordance with FIG. 4(a) when heat has been removed and the ends are permitted to cool.

FIGS. 5(a) through 5(c) show several different configurations of the light-receiving end of two optical fibers in the process of being flared and shaped. FIG. 5(a) is an end-on view of the optical fiber as fusion commences. FIG. 5(b) shows the proximal light-receiving end of the optical fiber being fused and flared. FIG. 5(c) shows the proximal light-receiving end of the fibers flared and fused for a longer period of time and/or at a higher temperature than the flared fibers shown in FIGS. 5(a) or 5(b FIGS. 5(d) and 5(e) show similar end on views of a plurality of optical fibers in the process of being fused and shaped to form a convex lens on the light-receiving end thereof In the multi-fiber flaring and fusing process, all optical fibers are being heated to fuse together to form a unitary mass and flare at the same time. Each fiber optic will form a larger end diametrically during the fusing process. Light-collecting characteristics of each of the plurality of fiber optics are individually improved, as a larger unitary lens-shaped terminus is formed on the composite fiber bundle.

For transillumination of tissue it may be desirable to adapt the distal, light delivery ends of the optical fibers to redirect axially directed light propagating through the fiber optic radially outward to form a particularly bright image. This can be achieved by compressing a portion of the fiber near the distal end thereof by means of a die having a central bore dimensioned to accommodate a fiber optic with one or more split rings projecting thereinto and coaxial with the bore. A tool suitable for compressing a circumferential annular groove into the wall of a fiber optic is shown in cross-section in FIG. 6. The tool 60 comprises a pair of steel plates 61 having a hole or bore 62 drilled herein. The bore is uniform in diameter except at the constricted central portion where the diameter of the bore is reduced to form an annular protuberance 64 within the bore and coaxial therewith centered on the parting line 65 of the plates 61. When the light delivery end of a fiber optic is placed within the bore 62 and the plates 61 are compressed, an annular groove 71 is depressed into the fiber optic as shown more clearly in FIG. 8. A transparent sheath 72, cutaway in FIGS. 7 and 8 for clarity, encloses the fibers individually over a portion of their length coextensive with the groove(s) and provides and maintains an air gap 73 overlying the grooves 71. Axially propagating light is refracted at the air/fiber interface to exit the fiber in a radial direction. More than one tool placed side by side may be used to create a plurality of annular grooves in the fiber.

While particular embodiments of the present invention have been illustrated and described, it would be obvious to those skilled in the art that various other changes and modifications can be made without departing from the spirit and scope of this invention. It is therefore intended to cover in the appended claims all such changes and modifications that are within the scope of this invention.

What we claim is:

1. A fiber optic light delivery catheter adapted for use with a light source having a light output port, said catheter comprising an elongate body portion having a proximal end and a distal end and a length therebetween and a plurality of discrete substantially parallel optical fibers coextensive with at least a portion of said length and having an optical axis parallel to said length, said proximal end of said plurality of optical fibers being fused to one another to form a unitary lens disposed adjacent to a light output port of a light source and adapted to receive light from said light output port of said light source and wherein said body portion is operable for conducting said received light from said proximal end of said catheter to said distal end.

2. The catheter of claim 1 wherein said proximal end of said plurality of fibers being fused is flared.

3. The catheter of claim 1 wherein a portion of said plurality of fiber optics adjacent said distal end is adapted to deliver diffuse light laterally therefrom.

4. The light delivery catheter of claim 1 wherein said catheter further comprises a transparent sheath overlying at least a portion of the length of said plurality of fiber optics.

5. The light delivery catheter of claim 2 wherein said catheter further comprises a transparent sheath overlying at least a portion of the length of said plurality of fiber optics.

* * * * *